Figure 1:
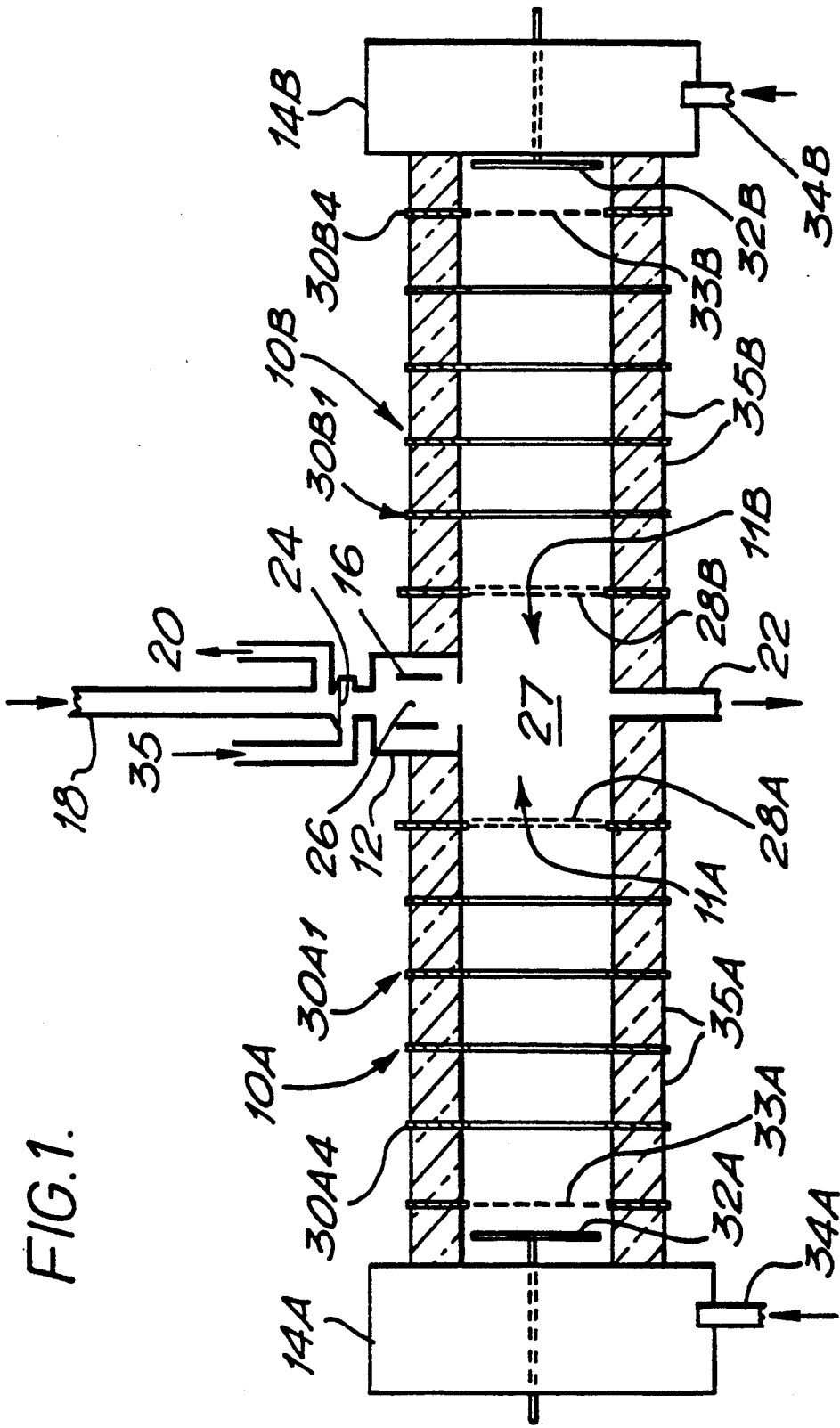

United States Patent [19]

Turner

[11] Patent Number: 5,227,628

[45] Date of Patent: Jul. 13, 1993

[54] ION MOBILITY DETECTOR

[75] Inventor: Brian R. Turner, Chesham, United Kingdom

[73] Assignee: Graseby Dynamics Limited, Cambridge, England

[21] Appl. No.: 741,472

[22] PCT Filed: Feb. 7, 1990

[86] PCT No.: PCT/GB90/00182

§ 371 Date: Aug. 5, 1991

§ 102(e) Date: Aug. 5, 1991

[87] PCT Pub. No.: WO90/09583

PCT Pub. Date: Aug. 23, 1990

[30] Foreign Application Priority Data

Feb. 9, 1989 [GB] United Kingdom ............... 8902920

[51] Int. Cl.⁵ .................... B01D 59/44; H01J 49/00
[52] U.S. Cl. ................... 250/286; 250/282; 250/287; 250/423 R
[58] Field of Search ............ 250/281, 282, 286, 287, 250/423 R

[56] References Cited

U.S. PATENT DOCUMENTS

| 4,378,499 | 3/1983 | Spangler et al. | 250/286 |
| 4,390,784 | 6/1983 | Browning et al. | 250/286 |
| 4,445,038 | 4/1984 | Spangler et al. | 250/287 |
| 4,855,595 | 8/1989 | Blanchard | 250/287 |
| 5,021,654 | 6/1991 | Campbell et al. | 250/287 |
| 5,070,240 | 12/1991 | Lee et al. | 250/286 |

Primary Examiner—Bruce C. Anderson
Attorney, Agent, or Firm—McAulay Fisher Nissen Goldberg & Kiel

[57] ABSTRACT

There is disclosed an ion mobility detector having a sample inlet membrane means for flowing a sample passing through the membrane over an ionisation source to an ion reaction region, with which two or more ion drift regions communicate, means for impressing a potential gradient on each drift region, an ion injection shutter at the entrance to each drift region whereby the drift region can be made accessible or inaccessible to ions of a particular sign located in the reaction region, an ion detector in each drift region, means for passing drift gas down each drift region to the reaction region and exit means in the reaction region remote from the ionisation source for venting drift gas from the reaction region, the ionisation source (26) being offset from the reaction region (27).

8 Claims, 3 Drawing Sheets

ION MOBILITY DETECTOR

This invention relates to ion mobility detectors.

Ion mobility detectors are used to detect the presence of materials in an environment, for example contaminants in atmospheric air. A library of known possible contaminants is built up and the measurements known for these are then compared with the results from an unknown species to decide whether a sample contains a contaminant and if so whether it has already been identified. Measurement of concentration or an indication of concentration can be given as well as qualitative identification of the species.

Typical prior art ion mobility detectors have an ionization source, an ion reaction region, an ion drift region, e.g. in the form of a tube, an ion injection shutter or grid interposed between the ion reaction region and the ion drift region, and an ion detector. The systems operate at atmospheric pressure where the mean free path of the contained gas molecules in the drift region is a small fraction of the dimensions of the container. A carrier gas, normally purified atmospheric air (particularly purified to remove water vapor which can interfere with the detection of certain types of charged species) is introduced into the ion mobility detector with a sample gas or vapor of the material whose identity is to be determined by characterization of its ion mobility properties. The carrier gas containing the sample is introduced through an inlet so as to be exposed to the ionization source. This causes portions of both the carrier gas and the sample to be directly ionized at the ionization source. The molecules of the carrier gas are present in far greater numbers than the sample and so more of these are ionized. The gaseous mixture is located within the reaction region at this stage and since the mean free path is many times smaller than the dimensions of the reaction region, multiple collisions between the molecules of the carrier and the sample gas(es) occur, the result of which is that the ion charge tends to be transferred by these collisions from the carrier molecules to the sample molecules thus resulting in a secondary ionization process which ionizes an increased number of the molecules of the sample. The reaction region is normally arranged to be under the influence of a potential gradient which moves the charged mixture towards the ion injection grid which is electrically charged to prevent transfer of ions from the reaction region to the drift region but which can be deenergized so as to let a pulse of ions pass through into the drift region. Accordingly, periodically the grid is de-energized for a short time and a number of ions are introduced into the drift region. This period is called the cycle time and can be varied. The drift region is arranged to be under the influence of an electrostatic drift field or potential gradient which acts to move ions in the drift region down the tube away from the ion injection grid towards a detector electrode which collects the charge from the ions and is located at the end of the drift region. The time of arrival of each ion at the detector grid relative to the time that the ion injection grid was opened is determined by the mobility of the ion in the carrier gas occupying the drift region. Heavier ions move more slowly through the drift region and take longer to travel to the detector than lighter ions. Ions with the same mobility have their velocities modified slightly due to diffusion effects; when they arrive at the detector electrode they are spread in an error function, the peak of which enables one to determine the time taken between the opening of the grid and arrival of the group at the detector. This can be used to characterize the ions.

However, some molecules which it is wished to detect ionize to form positive species and others form negative species and some form both species. If detection of both species could be simultaneously achieved on the same sample this would be attractive. Thus using a single conventional device a delay will be incurred in switching from positive to negative operating conditions and the measurements will not be done on precisely the same sample. If two separate drift cells are used the samples again will not be precisely the same.

U.S. Pat. No. 4,445,038 (Bendix) proposes a double tube arrangement to enable positive and negative species to be detected simultaneously. It proposes opposed drift tubes with an interposed ionizing source and a transverse flow of sample and carrier gas directed across the ionizing source. This necessitates the incorporation of a long sample inlet line leading from the inlet nozzle to an entrance located in the ionizing source mounted centrally between the opposed drift tubes. Experiments have shown that an offset ionizing source enables a faster response and greater sensitivity to be achieved.

Bendix suggest that the positive and negative ions can be detected by simultaneously opening the shutter grids on each tube or opening the grids sequentially. In the Bendix arrangement the potential field in tube 18 draws out positive ions from the ionization region and tube 16 negative ions. In order to get simultaneous positive and negative spectra the ionizer must be at a fixed potential.

According to a first aspect of the present invention an ion mobility detector has a sample inlet membrane, means for flowing a sample passing through the membrane over an ionization source to an ion reaction region, with which two or more ion drift regions communicate, means for impressing a potential gradient on each drift region, an ion injection shutter at the entrance to each drift region whereby the drift region can be made accessible or inaccessible to ions of a particular sign located in the reaction region, an ion detector in each drift region, means for passing drift gas down each drift region to the reaction region and exit means in the reaction region remote from the ionization source for venting drift gas from the reaction region, the ionization source being offset from the reaction region. The ionization region being offset from the reaction region gives the advantage that ionization of the carrier gas and sample can occur before they enter the reaction region.

Preferably the detector has two cylindrical drift regions, arranged to attract ions of opposite polarity, disposed at either end of a cylindrical reaction region and the ionization source is located in a housing outside the cylindrical reaction region, the said housing communicating with the reaction region. Preferably the exit means for venting the drift gas are diammetrically opposite the housing for the ionization source.

The offset ionizing source conveniently permits the sample to be introduced to the ionizing region via as short a path as possible. Minimizing this path length is essential if the instrument is to exhibit rapid responses to changes in sample concentration.

In addition the offset source permits a straight through gas flow arrangement. This arrangement has two advantages, firstly all the sample passes through all of the source, such an arrangement maximizes sensitivity, secondly the possibility of any sample molecules entering the drift regions is removed while retaining the facility to independently vary the gas flow, for example to change the sensitivity of the device.

According to a second aspect of the present invention an ion mobility detector is provided with an alternating potential to the ionization source. This aspect of the present invention may be used with ion mobility detectors having a number of drift tubes particularly the preferred two tube arrangements referred to in connection with the first aspect of the present invention.

The advantage of applying an alternating potential to the radioactive source is that it tends to remove the effects of surface charge build-up on the various components in the ionization and reaction regions. The concentration of ions in these regions is much greater than that in the rest of the device and, if a constant voltage is applied to the source, it is found that collision of ions with surfaces in this region leads, over a period of seconds or greater, to the build-up of charge on the surfaces. The disadvantage of this is that the electric field within the device is modified so as to repel ions away from the desired paths. The observed effect is a steady reduction in signal amplitude with time.

In the Bendix specification discussed above, Bendix makes no suggestion that the ionizing potential should be alternating. The use of an alternating potential on the source periodically floods the ionizing and reaction regions with ions of opposite polarity. Surface charges are thus neutralized and the ion currents through the drift tube or tubes are optimized. It will be appreciated that in a conventional ion mobility detector only a fraction of the ions reaching the shutter grids are admitted to the drift region to be analyzed, typically the shutter grid might be open for 1% of the time In this device we are using these spare ions for surface charge neutralization to ensure that when the grid or grids are open the maximum number of ions is admitted.

The alternating potential can be altered in frequency and amplitude; the rectangular waveform is preferably variable in symmetry with the respect to the positive and negative such that the duration and amplitude of the positive potential can be varied independently of the duration and amplitude of the negative potential. In this way ion residence times can be varied for ions in the reaction region enabling the target ion concentration to be maximized indepen-dently for positive and negative ions.

Where such alternating potential is used—preferably of square form a sample from the ionization and reaction regions can be allowed to enter the drift region by application of a short gate-opening pulse to the ion injection grid. The time delay between the start of one half-cycle of the alternating potential and the gate-opening pulse can be varied in a number of preliminary steps, and the consequent currents, detected at the detector electrode, stored in memory, until at the end of the preliminary steps, a preferred time delay for the gate-opening pulse is selected for subsequent testing as giving optimum results—at least for ions of a particular characteristic i.e. those on which the preliminary steps were carried out.

Separate time delays can be set in this way for the two halves of the alternating potential cycle and hence for positive and negative ions.

Thus in a preferred method of using an ion mobility detector utilizing the second aspect of the present invention and preferably the first aspect as well, and thus using not only an alternating potential on the ionization source but also a pair of opposed drift tubes, a sample from the reaction region is allowed to enter a drift region by application of a short gate opening pulse to the ion injection shutter or grid, the time delay between the start of one half-cycle of the alternating potential and the gate opening pulse is varied in a number of preliminary steps and the consequent currents, detected at the ion detector in the drift tube, are stored in memory, until at the end of the preliminary steps, a preferred time delay for the gate-opening pulse is selected for subsequent testing as giving optimum results, e.g. maximum amplitude of the ion peak being assessed, for the ions on which the preliminary steps were carried out.

The test is performed under the control of a microprocesser in a controller, which is preprogrammed to perform the preliminary steps and the subsequent testing.

The whole process need occupy no more than 1 second, but enables optimum measurement to be made for a particular—or target—ion peak.

A drift region of tubular configuration may be constructed of alternating rings of ceramic material and metal, these electrically conductive metal rings being called guard rings. The stack of rings is clamped together and sealed so as to make a gas tight tube. Devices of this type often enclose the stack of rings within an outer sealed envelope. The electrostatic drift field potential gradient is established by connecting adjacent guard rings to each other via a resistor and connecting the end guard rings to the terminals of a voltage source. The conductive rings afford a series of ascending voltage levels and the longitudinal axis of the tube coincides with the longitudinal axis of the electrostatic field which is thus established.

Such a conventional arrangement is referred to in U.S. Pat. No. 3,522,425 which discloses a "conventional" voltage divider 50 comprising a plurality of spaced circumferential conductive plates interconnected by resistors 52 and terminally connected to a lead 26 connectable to a battery source and to a grounded electrode 12 so as to provide a relatively uniform field gradient.

Other constructions may be used instead to establish the electrostatic field. Thus U.S. Pat. No. 4,390,784 proposes a drift tube consisting of a tube of ceramic or glass or other suitable nonconductive material, coated continuously along its internal surface with a thick film resistor composition.

We prefer to use a potential gradient in the range 150 to 350 volts per centimeter, desirably from about 225 to 275 e.g. about 250 volts per centimeter.

For considerations of safety, it is preferred that the sample injection part of the device is arranged to be held at or near earth potential, requiring the collector electrode at the other end of the tube, and the amplifier coupled to it, to be at an elevated negative or positive potential e.g. 1250 v or more.

In a preferred form of the invention the means for recording, indicating or further processing of the signal output of the amplifier are isolated from the elevated voltage. This may be achieved by using an isolation amplifier using capacitative coupling of a frequency-modulated signal or an optical system based on this principle; it is preferably achieved by converting the output signal of the amplifier to a light output of intensity proportional to the signal amplitude and linking it e.g. by a fiber optic coupling, to an optical input for the recording, indicating or processing means.

Figure 2:
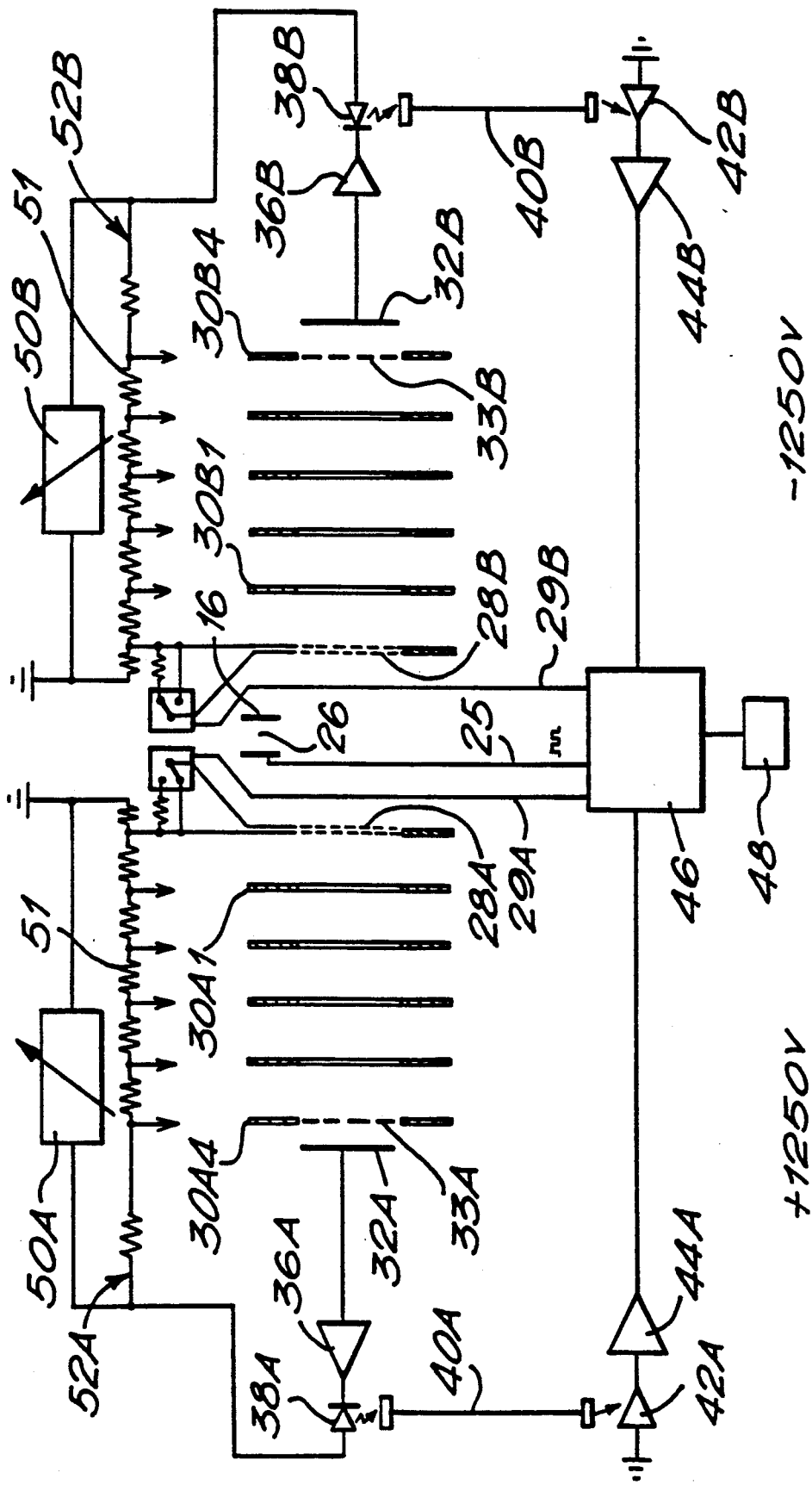
Figure 3:
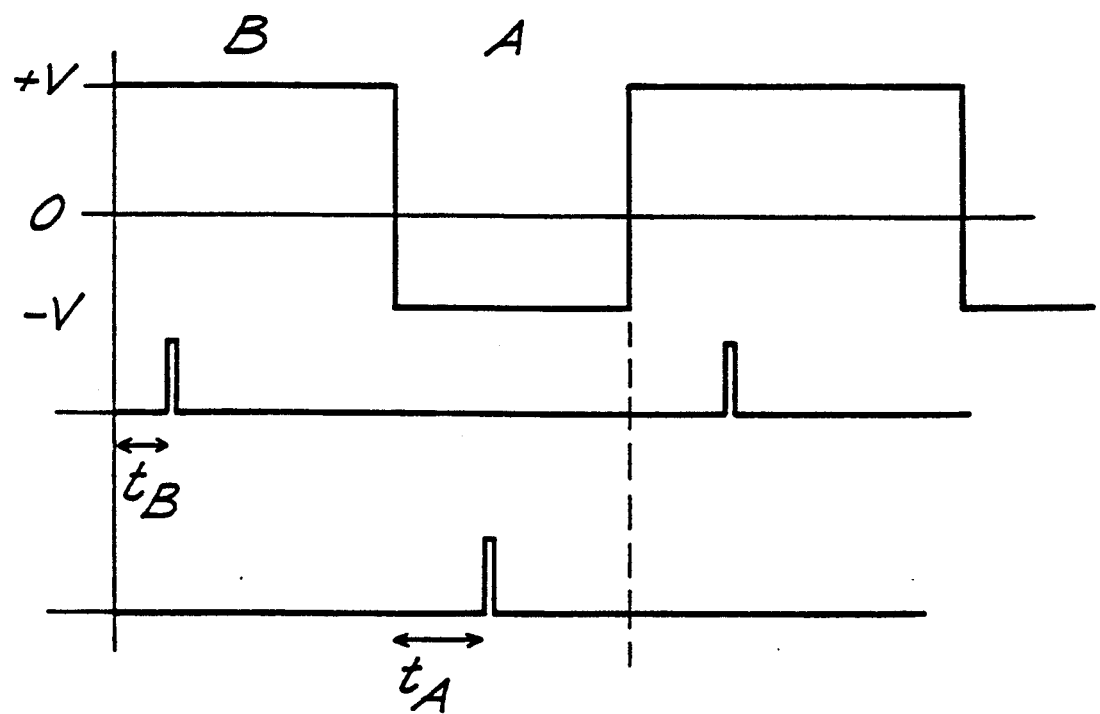

The invention may be put into practice in various ways and one specific embodiment will be described to illustrate the invention with reference to the accompanying diagrammatic representations in which:

FIG. 1 is a block schematic of an ion mobility detector showing the structure of the drift tubes and the gas flow paths of a device in accordance with the invention, FIG. 2 is a schematic block diagram (on a smaller scale) of the electrical connections and electronic components, and FIG. 3 is a representation of the rectangular wave form used in the invention Referring to FIGS. 1 and 2 an ion mobility detector has a pair of coaxial drift tubes 10A and 10B having their gating-grid ends 11A and 11B opposed to each other and defining a transversely disposed reaction region 27. The reaction region 27 is supplied with ionized species from an ionization region tube 16 which is located in a housing 12 offset to one side of the drift tubes 10A and 10B. Unipolar ions characteristic of the sample are generated in the reaction region tube 27 and the mobilities of the ions generated are determined in the drift tubes 10A and 10B. Each ion drift tube has an end cap 14A and 14B respectively. The housing 12 carries the ionization region tube 16 to one end, the inlet end, of which an inlet nozzle 18 carried by the housing 12 is juxtaposed. The interface between 12 and 18 is a membrane 24. The membrane end of nozzle 18 has a vent 20 to atmosphere to enable gases to vent to atmosphere. The ionization region tube 16 is adjacent at its inlet end to the membrane 24. An ionizing source 26 is disposed within the tube 16. The inlet ends 11A and 11B of each of the drift tubes are closed by grids 28A and 28B which thus define the side boundaries of the reaction region 27.

The tube 16 is a metal tube having an internal diameter of 7.4 mms. The injector grids 28A and 28B are mounted on ceramic rings which form ends of the drift tubes 10A and 10B. The grids 28A and 28B each consist of a so called fixed grid and a so called moving grid, the latter facing the reaction region 27.

Each drift tube is provided with a system for passing a counter flow of drift gas through it from the end caps 14A and 14B respectively to the reaction region 27. Each end cap 14 thus has a drift gas inlet 34A and 34B respectively. The reaction region has a drift gas outlet 22 disposed opposite the housing 12.

The ionization region tube 16 is also provided with an inlet 35 for a carrier gas (which may be the same as or different from the drift gas). The drift and carrier gases may be supplied from disposable sources e.g. pressurized cylinders of purified gas in known manner or may be connected to recirculating pumps, purifiers and driers so that the gases are conserved and held pure and of desired dryness, also in known manner.

Thus a flow of gas enters at the port 35, it picks up sample vapor permeating through the membrane 24, and carries it all through the full length of the radioactive source 26. In the region 27 the sample is diluted by the drift flows from the tubes 10A and 10B and the diluted sample flows pass out of the device through 22.

The end caps 14A and 14B also carry a collector electrode 32A and 32B respectively mounted within the drift tube 10A and 10B and preceded by a screen grid 33A and 33B respectively. The screen grids 33A and 33B are provided in order to overcome capacitive coupling and induced charge effects and are held at a constant potential relative to the collector such that the potential gradient in the space between the screen grid 33A and the collector electrode 32A is comparable with or greater than that in the rest of the drift tube.

The collector electrode has a diameter equal to the internal diameter of the drift tube.

Each drift tube 10A and 10B is provided with a structure for applying a potential gradient along the length of the tube. This structure consists of four spaced metal guard rings 30A1 to 30A4 and 30B1 to 30B4. The rings are spaced apart by ceramic discs along the tube, the whole stack being clamped together to form a tube in known manner.

An appropriate voltage is applied to each ring to establish the desired voltage gradient.

The voltages are applied by means of a pair of adjustable high voltage sources shown schematically in FIG. 2 as 50A and 50B bridged by a resistor chain again shown schematically as 52A and 52B. Each chain (made of resistors 51) is connected between the inlet nozzle assembly (which is held at zero potential) and the respective collector electrode 32A or 32B (one of which is at high positive and the other of which is at high negative potential e.g. +1250 and −1250 v).

For each chain 52 intermediate points are connected to the fixed grid of its gate 28 and the guard rings 30 of its drift tube 10 and to its collector grid 32 and its screen grid 33 and establish appropriate potential differences at these various locations in the detector.

The source 26 is preferably the well known $^{63}Ni$ foil radioactive source which produces beta radiation. A potential gradient is established as described below, from the source 26 to the grids 28A and 28B, acting to move the charged ions from the vicinity of the source to the injector grids 28A and 28B (32A being positive, the grid 28A is positive and attracts negative ions; 32B being negative, the grid 28B is negative and attracts positive ions) where, if the grid is closed, the respective ions are discharged. The precise mode of operation is described in more detail below.

The potential steps between the guard rings 30 of the drift tube are equal.

Each collector electrode 32A and 32B is connected to an amplifier 36A and 36B respectively which has an optical diode 38A and 38B respectively at its output. These diodes float at the same potential as the collector grids 32. Fiber optic links 40A and 40B couple the light output of the diodes 38A and 38B respectively to the input of diodes 42A and 42B at the input of amplifiers 44A and 44B the outputs of which are connected to the input of an electronic control unit 46. The control unit supplies an output to a recorder/indicator 48 and is arranged to provide trigger pulses to the injector grids 28A and 28B via the lines 29A and 29B.

Each injector grid 28 is normally biased electrically by the control unit 46 to prevent the passage of ions, but each is gated periodically by means of an electrical pulse from the control unit 46 to permit the gated injector grid 28 to pass a pulse of ions into the respective drift tube 10A or 10B.

The grids 28 are typically two sets of parallel, almost interdigitated wires. The grid is closed when a potential difference is applied between the two sets of wires. When there is no potential difference between the two sets of wires, e.g. when they are connected electrically, ions can flow through the grid. The grid affords a circular opening to the drift tube having a diameter of 12 mms.

The potential difference across the resistor chain from 18 to 32A is +1250 v and from 18 to 32B is −1250 v. The potential of the source 26 is preferably +250, but can be up to ±500 volts and it is spaced about 4 mms from the fixed grids of each grid 28 which are held at voltages, relative to that on source 26, such that the field gradient between the source and the fixed grid is approximately equal to that in the tubes 10 (which is typically 300 volts/cm). The moving grid of each injector grid 28 is held at a voltage above that of the fixed grid by the controller 46 e.g. 30, 40 or say 70 volts to hold the injection gate 28 closed. The controller 46 equalizes the voltages to open the gate. The resistors 51 between the conductors 30 are typically 5 megohms producing potentials at conductors 30A1 to conductor 30A4 such that an approximately linear field gradient of 300 volts/cm is created in tube 10A and in tube 10B.

The operation of the device is as follows. Drift tube gas, typically dried purified air, is circulated though each drift tube 10 entering at 34A and 34B and exiting at 22. Conventional flow rates known in the art are used e.g. 1 to 50 ccs of gas per cc of drift tube volume/minute.

The air is desirably zero air. The function of the drift gas is to quench ion-molecule reaction in the drift tube.

The carrier gas which in a typical use is ambient atmospheric air containing a gas sample to be detected and characterized is drawn into the inlet 18 by means of a pump (not shown) attached to the vent 20. Similar flow rates in relation to the volume of the reactant tube 30 may be used as for the drift gas. The membrane 24 is chosen to be selectively permeable to species which it is wished to detect such as organic molecules, while being much less permeable or essentially impermeable to $H_2O$, $O_2$, $N_2$ and $CO_2$. The species it is wished to detect thus permeate through the membrane into the ionization tube 16 and together with some of the carrier gas pass into the vicinity of the ionizing source 26. The membrane may comprise a sheet of silicone-based rubber material such as dimethyl silicone rubber. The voltage sources are switched on 50A being positive and 50B negative. The carrier gas molecules are ionized and to a lesser extent the sample species.

As the ion mobility detector operates at or near atmospheric pressure, the mean free path of the ions and other molecules is small in relation to the dimensions of the confining space and there are many collisions between the various gas molecules in the reaction region within the space 27. The collisions tend to produce ionized sample molecules by charge transfer from the ionized carrier gas molecules.

The field gradient between the ionizing source 26 and the injector grids 28 moves the ions generated by the ionizing source from the carrier and sample gas towards the injector grids 28.

The ion mobility detector in accordance with the invention can detect both positively-charged and negatively-charged ions virtually simultaneously. If as indicated above the potential at the collector grid 32A is arranged to be positive then negative ions will be attracted towards it, and collector 32B will be negative so that positive ions are attracted towards it.

The ionizing tube of $^{63}Ni$ foil is supplied with alternating current from a separate AC source under the control of the controller 46 via a line 25. This current is of rectangular wave form typically +250 v relative to ground with a frequency of up to 100 Hertz and typically 50 Hertz (50 cycles per second). As the potential at 26 switches to +250 v, the potential difference between 26 and the grid 28A causes the negative ions to move towards the grid 28A and they are discharged when they reach the grid 28A, if it is closed. The positive ions created by the $^{63}Ni$ foil are discharged at the tube 16 during this period of time.

The controller 46 generates the rectangular waveform, which may be asymmetric with respect to the positive- and negative-going portions, and triggers the gating grids to open after controlled delays from the rising edge of the rectangular wave as represented in FIG. 3. The positive or negative delays can be adjusted separately, either manually or in a feed-back loop, while monitoring the target ion peak in the positive or negative ion spectrum respectively.

In a first operation with the time delay, $t_B$ (see FIG. 3), short, the detector current from the collector 32B by way of the link 36B, 38B, 40B, 42B and 44B, is fed to the controller 46 and retained in memory there as a current time spectrum starting from the time of the gate opening pulse at $t_B$ and showing detected current peaks at times-from-starting and amplitudes respectively representing the characteristics of the ions in a package and the number of ions with that characteristic.

In the next operation, the time delay $t_B$ is increased, and a further current/time spectrum is stored in memory.

The time delay $t_B$ is increased in steps over its range within the positive half of the square wave.

The controller 46 is programmed to select for subsequent use the particular time delay $t_B$ which gave the maximum current amplitudes in a specified peak.

In successive steps using the selected time delay $t_B$, detected currents are averaged and used for record or display. The whole process may take from 0.5 to 1.0 seconds.

The process is repeated for the time delay $t_A$ and the negative ions.

The interval between the top of successive rising edges is typically 20 milliseconds (ms). The gating grids may be opened for 50–1000 microseconds (us), but preferably about 180 microseconds (us) and this gating time represents the beginning of the drift time for the slab of negative ions, in the case of grid 28A or the slab of positive ions, in the case of grid 28B.

When the AC potential switches to −250 v the positive mode delay is initiated permitting the build up of positive current in the injection region 27; at the end of this delay period the controller 46 opens the injector grid 28B for a short period typically 180 microseconds (us) (this is the beginning of the drift time for this slab or batch of positive ions). The grid 28B is opened typically about 10 ms after the gate 28A and by this time the first batch of negative ions are about half-way down the tube 10A.

This cycle is repeated and the readings averaged by the controller 46 for the positive and negative collector currents to give averaged values. Typically the number of cycles is 16, but this can be varied in order to achieve appropriate signal-to-noise ratio.

The amplitude of the rectangular wave can be varied if desired and may have an amplitude as great as ±500 v.

Increasing the amplitude decreases the residence time of ions in the ionization and reaction regions and enables, via a variety of ion-molecule reactions, the target ion concentration to be maximized.

The beta particles from the Ni$^{63}$ source collide with mainly carrier gas molecules and produce positive/negative ion pairs. When the source is at positive potential, the positive ions are discharged at the source and the negative ions are repelled into the reaction region where they undergo further ion-molecule reactions including charge exchange and addition reactions. A simple example is when an $O_2^-$ ion collides with an appropriate sample molecule M a charge exchange can occur producing a charged sample as $O_2^- + M = O_2 + m^-$, and subsequently other $M^-$ related adduct ions.

It is these product ions which are drawn from the reaction region 27 to the grid 28A.

The injector grid is opened, by the controller 46 removing the potential, typically for about 0.18 milliseconds (ms) every 20 ms thus introducing a regular pulse or slice of negatively charged ions into the drift tube 10A. This time interval of 20 ms is known as the cycle time. In this arrangement the cycle time can be varied as desired between 10 and 1000 ms. As mentioned above the counterflowing drift tube gas has the function of quenching any further reactions between the ions and molecules.

The ions then are moved down the tube by the applied even electrostatic field to the collector 32A and as they pass down the tube 10A they separate into faster more mobile negative ions followed by slower less mobile negative ions and each group arrives at the electrode as a distribution around a mean or peak maximum which is used to identify the mobility of the particular negative ion species. The ions thus tend to separate into discrete mobility groups, the groups reaching the collector electrode 32A at discrete times after their injection into the drift tube by the injector grid 28A the drift times being directly related to ion mobilities.

The ions are discharged at the collector electrode 32A and this generates an electrical current at the input to the amplifier 36A related to the number of ions in each group as it strikes the electrode 32A.

The current is amplified by the amplifier 36A producing related variations in the intensity of the light emitted by the light emitting diode 38A.

The emitted light is coupled by the fiber-optic coupling 40A to the diode 42A which generates a related current at the input of the amplifier 44A, which is amplified and passed to the control unit 46 and, after processing, to the indicator/recorder 48, which may be an oscilloscope, pen recorder, magnetic storage medium or alarm or any combination of these.

The construction, circuitry and mode of operation of the controller 46 are otherwise as described earlier.

The current signal from the electronic control unit 46 to the indicator/recorder 48 can be an ion mobility spectrum which can be calibrated in ion mobility and related to the quantity and type of molecules present in the atmosphere sampled by the inlet nozzle 18.

The counter flow of drift gas through the tubes 10A and 10B serves to remove non-ionized molecules of sample and carrier which may have passed through the injector electrodes 28A and 28B and which could, if not removed, cause further ion-molecule reactions to occur which may change the identity of the ions, as detected at the collector, during transit through the drift region and result in distortion of the ion mobility spectrum.

As mentioned above some molecules ionise into a single ion species, others into a number of ion species. The time of arrival and size of these peaks and their sign can be used as a characteristic spectrum by which an unknown species can be correlated with a known sample, provided that the drift conditions are known i.e. potential, carrier gas, value of flow rate, purity, temperature, pressure and humidity.

The controller 46 preferably thus contains a library of spectra for known species. These can be displayed on the recorder-display 48 and compared with the unknown sample or the comparison can be done in the controller and when a fit is detected the name of the detected species then displayed or some characteristic signal, visual or audible or both, given.

In addition the concentration of the detected species can be measured and a direct numerical read out or merely an indication of concentration levels given.

As indicated above the grids 28 are pulsed every cycle which as mentioned above may be in the range 10 to 1000 ms. The collector electrode 32 measures the ion peak pattern continuously, the amplitude of the pulse being proportional to the number of ions, the ion arrival time being characteristic of the ion. Thus the actual drift time of the ion is the time base and a complete ion drift pattern is generated in each cycle. It can take a few seconds for the sample to clear the cell thus averaging repetitive scans over a number of cycles (as mentioned above) can help obtain an improved signal to noise ratio.

I claim:

1. In an ion mobility detector having first and second ion drift regions, each communicating with an ion reaction region, the improvement comprising:
   an ionization region offset from said ion reaction region, said ionization region containing an ionization source.

2. The detector improvement of claim 1 further comprising:
   a source of alternating potential connected to said ionization source.

3. The detector improvement of claim 1 wherein:
   said ionization region comprises a housing adjacent to and in communication with said ion reaction region and containing said ionization source.

4. The detector improvement of claim 3 further comprising:
   a source of alternating potential connected to said ionization source.

5. In an ion mobility detector having an ionization region containing an ionization source, the improvement comprising:
   a souce of alternating potential connected to said ionization source.

6. In an ion mobility detector having a sample inlet membrane, means for passing a sample through the membrane and over an ionization source and into an ion reaction region, two or more ion drift regions communicating with the ion reaction region, means for impressing a potential gradient on each drift region, an ion injection shutter at the entrance to each drift region for making each drift region accessible or inaccessible to ions of a particular sign located in the ion reaction region, an ion detector in each drift region, means for passing drift gas down each drift region to the ion reaction region and exit means in the ion reaction region remote from the ionization source for venting drift gas from the ion reaction region, the improvement comprising:

an ionization region offset from said ion reaction region, said ionization region containing an ionization source.

7. The detector improvement of claim 6 wherein said drift regions comprise:
first and second cylindrical drift regions disposed at opposite ends of a cylindrical reaction region,
said first drift region attracting ions having a first polarity and said second drift region attracting ions having a second polarity.

8. A method of using an ion mobility detector which has a sample inlet membrane, means for passing a sample through the membrane, over an ionization source to which an alternating potential is applied and into an ion reaction region, at least one ion drift region communicating with the ion reaction region, means for impressing a potential gradient on the drift region, an ion injection shutter at the entrance to the drift region for making the drift region accessible or inaccessible to ions of a particular sign located in the ion reaction region, an ion detector in each drift tube, means for passing drift gas down the drift tube to the ion reaction region and exit means in the ion reaction region for venting drift gas from the ion reaction region, the method comprising the steps of:
introducing a sample into the reaction region,
applying a short gate opening pulse to the ion injection shutter, thereby allowing at least a portion of said sample from said reaction region to enter a drift region,
varying the time delay between the start of one half-cycle of the alternating potential and the gate opening pulse in a number of preliminary steps,
detecting the consequent currents at the ion detector in the drift region,
storing said detected currents in memory,
at the end of said preliminary steps, choosing a desired optimum characteristic of the ions of said sample,
selecting a time delay for the gate-opening pulse which yielded said chosen desired optimum characteristic for the ions of the sample, and
using said selected time delay for subsequent testing of the ions of the sample.

* * * * *